United States Patent [19]

Jäger

[11] 4,143,206
[45] Mar. 6, 1979

[54] METHOD OF FINISHING SYNTHETIC ORGANIC FIBROUS MATERIAL, IN PARTICULAR OF PROVIDING IT WITH AN ANTISTATIC FINISH

[75] Inventor: Horst Jäger, Bettingen, Switzerland

[73] Assignee: Ciba-Geigy Corporation, Ardsley, N.Y.

[21] Appl. No.: 833,832

[22] Filed: Sep. 16, 1977

Related U.S. Application Data

[62] Division of Ser. No. 639,312, Dec. 10, 1975, Pat. No. 4,066,597.

[30] Foreign Application Priority Data

Dec. 20, 1974 [CH] Switzerland ............... 17038/74
Dec. 20, 1974 [CH] Switzerland ............... 17037/74
Dec. 20, 1974 [CH] Switzerland ............... 17036/74

[51] Int. Cl.² ............ B05D 3/02; B32B 27/06; B32B 27/34; B32B 27/00
[52] U.S. Cl. ............... 428/474; 427/390 B; 427/390 E; 428/500
[58] Field of Search ............. 8/116 P; 260/29.4 UA, 260/29.6 TA, 29.6 HN, 29.6 WB, 32.8 R, 33.8 UA, 874, 898, 29.6 RW, 899, 901; 427/390 E, 390 B; 526/274; 428/474, 500

[56] References Cited

U.S. PATENT DOCUMENTS

| 3,350,336 | 10/1967 | Kelley | 260/22 CB |
|---|---|---|---|
| 3,385,914 | 5/1968 | Hindersinn et al. | 260/944 |
| 3,839,207 | 10/1974 | Weil | 8/116 X |
| 3,884,629 | 5/1975 | Duffy | 8/116 P |
| 3,900,665 | 8/1975 | Weil | 8/116 X |

Primary Examiner—Michael R. Lusignan
Attorney, Agent, or Firm—Prabodh I. Almaula

[57] ABSTRACT

A method of finishing synthetic organic fibrous material, in particular of providing such material with an antistatic finish and simultaneously improving the dirt repellency is provided, which comprises treating said material with aqueous or organic solutions or emulsions which contain (a) at least one copolymer derived from at least two of the monomers of formulae

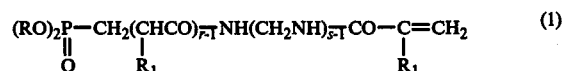 (1)

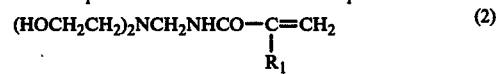

(2)

and

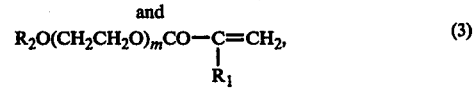 (3)

wherein R is straight-chain or branched alkyl of 1 to 8 carbon atoms, $R_1$ is hydrogen or methyl, $R_2$ is alkyl of 1 to 6 carbon atoms, m is an integer from 6 to 15, and each of $r$ and $s$ is 1 or 2, or a copolymer of the above monomers and further ethylenically unsaturated monomers, optionally in admixture with further homo- or copolymers and/or monomeric compounds. The furnish synthetic organic fibrous material, especially textile material, shows a permanent antistatic effect. The antisoiling effect and also the fastness to rubbing and light and the soft handle are not impared by the finish.

21 Claims, No Drawings

METHOD OF FINISHING SYNTHETIC ORGANIC FIBROUS MATERIAL, IN PARTICULAR OF PROVIDING IT WITH AN ANTISTATIC FINISH

This is a division of application Ser. No. 639,312, filed on Dec. 10, 1975, now U.S. Pat. No. 4,066,597, patented Jan. 3, 1978.

It is known to provide synthetic organic fibrous material with an antistatic or also dirt repellent finish. It is also known that a marked deterioration of the antisoiling effect occurs in many antistatic finishes. A further frequently observed disadvantage is the poor resistance to yellowing on exposure to light and/or heat.

To overcome these disadvantages in large measure it is the object of the present invention to provide preparations or compositions with antistatic properties for appropriate finishing procedures.

The present invention therefore provides a method of finishing synthetic organic fibrous material, in particular of providing such material with an antistatic finish and simultaneously improving the dirt repellency, which comprises treating said material with aqueous or organic solutions or emulsions which contain (a) at least one copolymer derived from at least two of the monomers of formulae

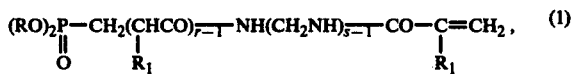  (1)

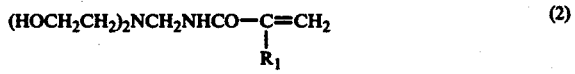  (2)

and

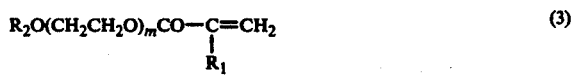  (3)

wherein R is straight-chain or branched alkyl of 1 to 8 carbon atoms, $R_1$ is hydrogen or methyl, $R_2$ is alkyl of 1 to 6 carbon atoms, $m$ is an integer from 6 to 15, and each of $r$ and $s$ is 1 or 2, or a copolymer of the above monomers and further ethylenically unsaturated monomers, optionally in admixture with at least one of the components ($b_1$) a homopolymer derived from the monomers of formulae (1) to (3), ($b_2$) a further homopolymer or copolymer, ($b_3$) a compound of formula

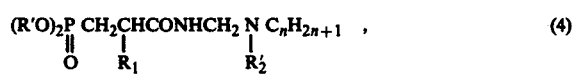  (4)

wherein R' is straight-chain or branched alkyl of 1 to 18 carbon atoms, $R_1$ is hydrogen or methyl, $R_2'$ is hydrogen or $C_nH_{2n+1}$ and $n$ is an integer from 1 to 24, and ($b_4$) a compound of formula

  (5)

wherein R" is

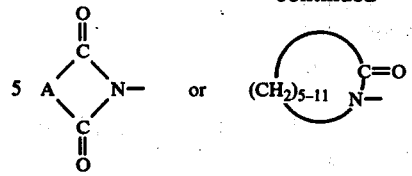

in which A is —CH$_2$CH$_2$—,

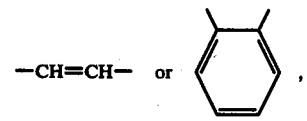

$R_3'$ is hydrogen or $C_nH_{2n+1}$- and $n$ is an integer from 1 to 24, and subsequently drying it at elevated temperature.

It is also a further object of the invention to provide the preparations for carrying out the method of application.

The homopolymers and copolymers (a), ($b_1$) and ($b_2$) can have molecular weights of about 2000 to 50,000.

The monomers of formulae (1) to (3) are known compounds. The compounds of formula (1) are known, for example, from Swiss patent 445,126 and German Offenlegungsschrift 2,215,434 (N-phosphonomethylacrylic amides), the compounds of formula (2) from German Auslegeschrift 1,111,825, and the compounds of formula (3) from U.S. Pat. No. 2,839,430.

It is preferred to use copolymers or mixtures of copolymers derived from the monomers of formulae (1), or (6) and (7), and (2); or (1), or (6) and (7), and (3); or (2) and (3); or copolymers derived from the cited monomers and further ethylenically unsaturated monomers. These copolymers (a) can, optionally, also be mixed with ($b_1$) homopolymers derived from the monomers of formulae (1), or (6) and (7), or (2) or (3), or also with ($b_2$) further homopolymers or copolymers. Where mixtures of copolymers obtained from at least two monomers of formulae (1), or (6) and (7); (2) and (3) are used, the mixture ratio can vary within wide limits and be about 1:10 to 10:1. More or less the same ratios apply to mixtures of homopolymers which can be additionally used.

The monomers of formula (1) preferably have the formulae

  (6)

and

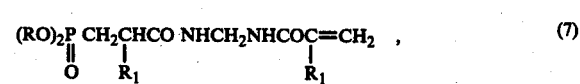  (7)

wherein R and $R_1$ are as previously defined, or especially the formulae

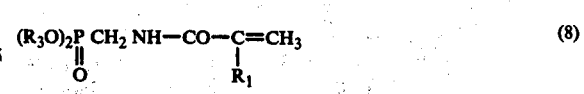  (8)

and

(9)

wherein $R_1$ is hydrogen or methyl and $R_3$ is alkyl of 1 to 4 carbon atoms. The compounds of the following formulae may be cited as examples:

(10)

(11)

(12)

(13)

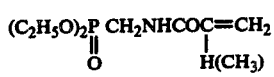

(14)

Preferred substituents $R_3$ are methyl and ethyl. Particularly suitable compounds of formulae (2) and (3) are those of formulae

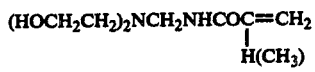

(15)

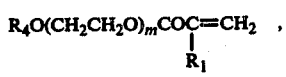

(16)

wherein $R_1$ is hydrogen or methyl, $R_4$ is alkyl of 1 to 4 carbon atoms, preferably methyl or ethyl, and $m$ is an integer from 6 to 15, for example from 6 to 10 ($m_1$) and from 10 to 15 ($m_2$), as indicated for example in the following formulae

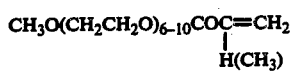

(17)

Examples of suitable comonomer components for the manufacture of copolymers derived from the monomers of formulae (1) to (3), and also for obtaining the further homopolymers which are not derived from the monomers of formulae (1) to (3), are:

(a) vinyl esters of organic acids, for example vinyl acetate, vinyl formiate, vinyl butyrate, vinyl benzoate,
(b) vinyl alkyl ketones, such as vinyl methyl ketone,
(c) vinyl halides, such as vinyl chloride, vinyl fluoride, vinylidene chloride,
(d) derivatives of the acrylic acid series, such as acrylic nitrile or acrylic amide and preferably derivatives thereof which are substituted at the amide nitrogen, for example N-methylolacrylic amide, N-methylolacrylic amide alkyl ethers, for example methylolacrylic amide monomethyl ether, N,N-dihydroxy-ethylacrylic amide, N-tert. butylacrylic amide and hexamethylolmelamine triacrylic amide, and (e) α,β-unsaturated mono- or dicarboxylic acids containing 3 to 5 carbon atoms and esters thereof, for example acrylic acid, methacrylic acid, α-chloroacrylic acid, crotonic acid, maleic acid, fumaric acid, or itaconic acid and esters thereof with mono- or dialcohols containing 1 to 18 carbon atoms, epoxides or phenols, for example ethyl acrylate, methylmethacrylate, glycidyl acrylate, butylacrylate, isobutylacrylate, acrylic acid monoglycol ester, dodecylacrylate or 2-ethyl-hexylacrylate, 3-tolyl-2(1)hydroxypropyl-1(2)-methacrylate or 2(1)-phenylphenolsulphone-1(2)-hydroxypropylmethacrylate.

Polymerisable olefins, such as isobutylene, butadiene or 2-chlorobutadiene or also styrene can also be used.

It is preferred to use acrylic acid, methacrylic acid, the esters thereof with 1 to 18, especially with 1 to 8, carbon atoms in the ester moiety, for example methylmethacrylate, isobutylacrylate, 2-ethylhexylacrylate, as well as acrylic amide and methacrylic amide, which can be N-methylolated and optionally etherified, for example N-methylolacrylic amide, N-methylolacrylic amide methyl ether.

The manufacture of the polymers by homo- or copolymerisation is effected by conventional methods, for example preferably by polymerisation in aqueous emulsion or also by solvent polymerisation in a solvent suitable for this purpose, for example acetone, benzene, sym. dichloroethane, ethyl acetate or trifluoromethylbenzene.

The polymerisation is effected advantageously with the application of heat, preferably to the boiling temperature of the solvent, and accompanied by the addition of peroxide or other catalysts which form free radicals and which are soluble in the reaction medium, for example benzoyl peroxide, lauroyl peroxide, α,α'-azobisisobutyrodinitrile or potassium sulphate or in the presence of redox systems, for example potassium peroxide disulphate/sodium bisulphite or ferrosulphate. In the manufacture of copolymers, the monomers can be used in the polymerisation reaction in any desired quantity ratios. In the manufacture of copolymers from, for example, monomer components, the molar ratio can be for example 1:10 to 10:1, preferably 1:5 to 5:1.

Depending on the nature of the polymerisation conditions and of the monomeric starting materials used, the polymer compounds are obtained in the form of viscous solutions or of emulsions.

The polymerisation is preferably carried out within a reaction time that is so chosen that a virtually quantitative conversion of the monomer into the polymer is attained. The maximum reaction time depends on the catalyst used and the polymerisation temperature and also on other conditions, but it is generally in the range of 0.5 to 24 hours.

The polymerisation temperature depends in turn on the chosen catalyst. In the case of emulsion polymerisation in aqueous medium it is usually in the range of 20° to 90° C. preferably 40° to 80° C. Wherever possible the polymerisation is carried out at atmospheric pressure.

In emulsion polymerisation the monomer or monomers to be polymerised are polymerised jointly in an aqueous solution of an emulsifier, where required under nitrogen.

The concentration of the polymerisation catalyst is usually between 0.1 and 2%, referred to the weight of the monomers.

Suitable emulsifiers are cationic, anionic or nonionic surface-active agents. The hydrophobic constituent of the emulsifier can be a hydrocarbon or a fluorinated hydrocarbon.

Suitable cationic emulsifiers are, for example, quaternary ammonium salts or amine salts which contain at least one long-chain alkyl or fluoroalkyl group, or a benzene or naphthalene group which is highly substituted by alkyl to yield the hydrophobic constituent.

Further suitable emulsifiers are the non-ionic surfactants in which the hydrophilic constituent is a poly(ethoxy) group and the hydrophobic constituent is either a hydrocarbon or a fluorinated hydrocarbon group, e.g. the ethylene oxide condensates of alkylphenols, alkanols, alkylamines, alkylthiols, alkylcarboxylic acids, fluoroalkylcarboxylic acids, fluoroalkylamides and the like. Anionic emulsifiers are, for example, the sulphuric acid or phosphoric acid esters of the cited ethylene oxide condensates of long-chain alkylphenols, fatty alcohols, and fatty amines.

In the solvent polymerisation, the monomer or monomers are dissolved in a suitable solvent, such as fluorinated solvents, for example hexafluoroxylene, benzotrifluoride, or mixtures thereof with acetone and/or ethyl acetate, and polymerised in a reaction vessel with the addition of initiators, such as azobisisobutyronitrile or other azo initiators, in concentrations of 0.1 to 2%, at 40° to 100° C., optionally under nitrogen.

Preferred solvents are hexafluoroxylene, benzotrifluoride or fluorinated hydrocarbons.

In the compounds of formula (4) [component (b$_3$)], which can, optionally, be used in the method of application of the present invention, the substituent R' is a straight-chain or branched alkyl radical of 1 to 18 carbon atoms, preferably of 1 to 4 carbon atoms, for example methyl, ethyl, propyl, isopropyl, butyl or isobutyl.

Examples of further alkyl radicals are: amyl, hexyl, octyl, decyl, dodecyl, myristyl, palmityl or stearyl. The substituent R$_2$' is hydrogen or the alkyl radical C$_n$H$_{2n+1}$ and n is an integer from 1 to 24, in particular from 6 to 24 and preferably from 6 to 18 or 8 to 18.

Preferred compounds of formula (4) are those, for example, of formula

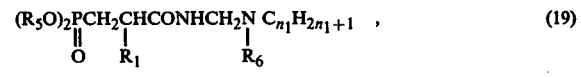  (19)

wherein R$_5$ is alkyl of 1 to 4 carbon atoms, R$_1$ is hydrogen or methyl, R$_6$ is hydrogen, methyl or the radical C$_{n_1}$H$_{2n_1+1}$ and $n_1$ is an integer from 6 to 24, in particular from 6 to 18.

Particularly suitable compounds are also those of formula

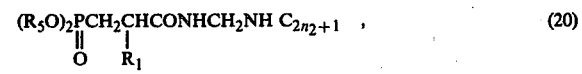  (20)

wherein R$_1$ and R$_5$ are as defined hereinbefore and $n_2$ is an integer from 6 to 18, in particular from 8 to 18.

The compounds of formula (4) are obtained, for example, by reacting methylolated-β-(dialkylphosphone)-propionic acid amides of formula

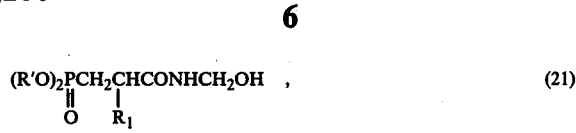  (21)

wherein R' and R$_1$ are as defined hereinbefore, with monoalkyl- or dialkylamines which contain 1 to 24 carbon atoms in the alkyl moiety, at elevated temperature.

The compounds of formulae (19) and (20) are also obtained in analogous manner.

The methylolated β-(dialkylphosphone)-propionic acid amides of formula (21) used as starting compounds are obtained by known methods, for example by addition of dialkylphosphites to (meth)acrylic amides and subsequent methylolation.

The manufacture of the compounds of formula (4) can be effected, for example, without solvents or in organic solvents, or also in organic aqueous systems, by reacting the cited starting materials at 80° to 120° C. The reaction time can be about 3 to 4 hours. Suitable solvents are, for example, halogenated hydrocarbons, such as tetrachloromethane, perchloroethylene, trichloroethylene, ethers, for example dioxan, or conventional aromatic solvents, for example benzene, toluene or xylene. The solvents can contain up to 20% of water, referred to their volume.

The compounds of formula (5) [component (b$_4$)], which are optionally used, preferably have the formulae

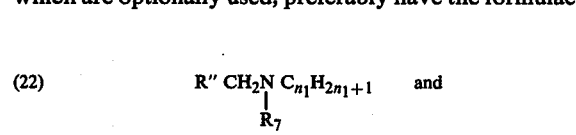

wherein R" is as defined hereinbefore, $n_1$ is an integer from 6 to 24 and $n_2$ is an integer from 6 to 18 or 12 to 18, and R$_7$ is hydrogen, methyl or C$_{n_1}$H$_{2n_1+1}$.

Examples of compounds of formula (5) are

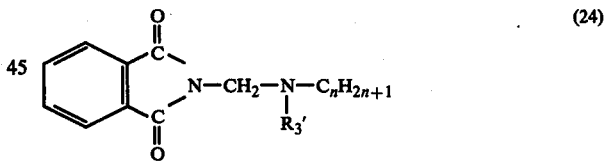  (24)

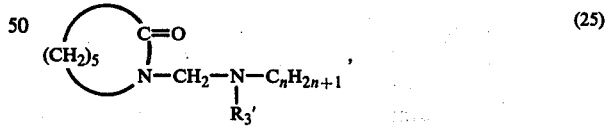  (25)

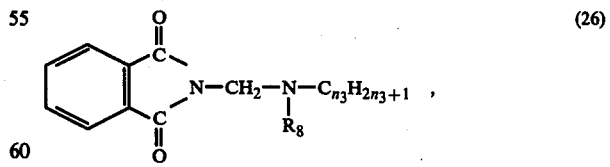  (26)

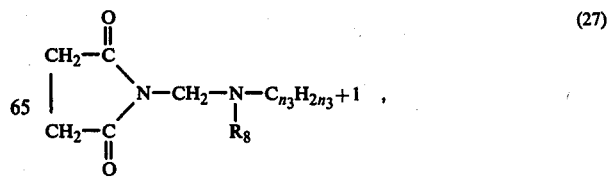  (27)

-continued

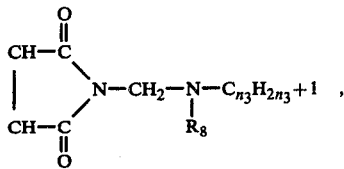 (28)

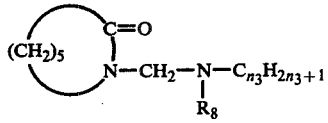 (29)

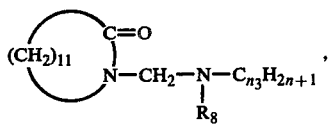 (30)

wherein $R_3'$ and $n$ are as defined hereinbefore, $R_8$ is hydrogen, methyl or $C_{n_3}H_{2n_3+1}$ and $n_3$ is an integer from 8 to 18.

The compounds of formulae (5) and (23) to (30) are obtained by known methods by addition of formaldehyde to succinimides, maleinimides or lactams and subsequent reaction with monoalkyl- or dialkylamines which contain 1 to 24 carbon atoms in the alkyl moiety. Examples of amines are laurylamine (of 12 carbon atoms) and cetylamine (of 16 carbon atoms), and also dilaurylamine, distearylamine (of 18 carbon atoms) and di-2-ethylhexylamine.

The preparations or compositions for carrying out the method of application of the invention, which are in the form of organic solutions or emulsions, contain as a rule 1 to 30 percent by weight of (a) at least one copolymer derived from at least two of the monomers of formulae (1) to (3), or of a copolymer of the indicated monomers and further ethylenically unsaturated monomers, optionally in admixture with at least one of the components ($b_1$) a homopolymer of the monomers (1) to (3), ($b_2$) a further homopolymer or copolymer, ($b_3$) a compound of formula

 (4)

wherein R' is straight-chain or branched alkyl of 1 to 18 carbon atoms, $R_1$ is hydrogen or methyl, $R_2'$ is hydrogen or $C_nH_{2n+1}$ and $n$ is an integer from 1 to 24, and ($b_4$) a compound of formula (5) 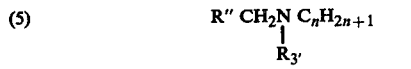

wherein R″ is

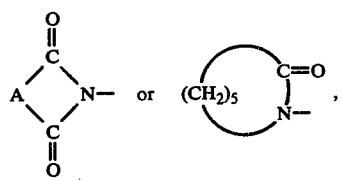

in which A is —CH₂CH₂—,

—CH=CH— or <span>(benzene ring)</span>, $R_3'$ is hydrogen or $C_nH_{2n+1}$ and $n$ is an integer from 1 to 24.

The indicated percentages by weight refer to the total weight of the preparation or composition. The total amount of polymers in the preparations should therefore not exceed 30 percent by weight, preferably about 20 percent by weight, whereas the amount of homopolymers or copolymers or of the compounds of components ($b_1$) to ($b_4$), if they are used, can be 1 to 10 percent by weight.

The preparations for providing synthetic organic material with an antistatic and dirt repellent finish therefore contain, for example, 1 to 30, in particular 1 to 20 and preferably 1 to 10, percent by weight of at least one copolymer (a), and optionally 1 to 10, preferably 1 to 5, percent by weight of components ($b_1$) to ($b_4$). The amount of copolymer (a) is preferably 75 to 100 percent by weight, so that components ($b_1$) to ($b_4$) (polymeric or monomeric compounds) are used in amounts of 25 to 0 percent by weight.

Suitable types of synthetic organic textile material that can be treated with the monomeric or polymeric compounds are those, for example, obtained from polyamides, polyesters, polyacrylonitrile or polyolefins. It is also possible to finish with advantage blends of these materials, optionally together with other fibres, for example cotton or wool. The textiles can be in the form of threads, fibres, flocks, non-wovens, woven or knitted fabrics or of piece goods, for example floor coverings, or other domestic textiles, such as upholstery fabrics, furnishing materials, curtains or wall coverings. The textile materials can be undyed or dyed by known methods.

The preparations or compositions which contain the monomeric or polymeric compounds can be applied to the substrate in conventional known manner at room temperature or also at elevated temperature, for example at 20° to 40° C. They can also contain further additives customarily used in textile finishing. The pH-value of the preparations can be about 2 to 10, preferably 5 to 8.

The substrates can be treated with solutions or emulsions of the polymers or of the indicated mixtures. The emulsions are prepared by adding customary and known surface-active assistants (emulsifiers).

Fabrics can be impregnated, for example, by the exhaustion process or on a padder that is coated with the preparation at room temperature. The impregnated material is subsequently dried at 80° to 200° C., preferably at 120° to 160° C. The fixation on the substrates can be effected, if desired, in the presence of conventional catalysts that split off acid, for example magnesium chloride or zinc nitrate.

Further methods of application are, for example, spraying, brushing roller coating or slop-padding. The compounds of the present invention are applied to the substrate in amounts of 0.1 to 10, preferably of 0.5 to 5, percent by weight.

The textile material finished according to the invention is antistatic, i.e. it releases no troublesome electrical discharges on being touched or walked on. The antisoiling effect and also the fastness to rubbing and light and the soft handle are not impaired by the finish.

The finish also has good permanency, i.e. it is resistant to washes with conventional household detergents or to cleaning with customary organic solvents. Carpeting materials, for example, can be repeatedly brushed, vacuum cleaned or shampooed without any impairment of the finishing effects.

The following Manufacturing Directions and Examples illustrate the present invention in more detail without implying any restriction to what is described therein. The parts and percentages are by weight unless otherwise indicated.

Manufacturing Directions 1a) 211 g (1 mole) of N-methylol-β-methoxyphosphonopropionic acid amide are dissolved in 50 ml of water and the solution is treated with 85 g (0.1 mole) of methacrylic amide and 0.2 g of hydroquinone monomethyl ether. The reaction solution is adjusted to a pH of 3 with 1 ml of concentrated hydrochloric acid and subsequently stirred for 6 hours at 50° C. Upon termination of the reaction, the reaction solution is adjusted to pH 7 with 2 ml of normal sodium hydroxide solution and filtered, to give 340 g of a 84% solution of the compound of formula

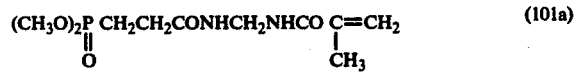
(101a)

in 100% yield.
Analysis: calculated: P 11.0 found: P 11.0
Mass spectrum: M = 278 (theory: 278).
1b) Example 1a) is repeated with acrylic amide to give the compound of formula

(101b)

in 98% yield.
Analysis: calculated: P 11.74 found: P 11.6
Mass spectrum: M = 264 (theory: 264).
(2) 133.5 g (0.5 mole) of N-methylol-β-diisopropoxyphosphonopropionic acid amide are reacted with 35.5 g (0.5 mole) of acrylic amide or 42.5 g (0.5 mole of methacrylic amide as in Direction 1a), to give the compounds of formulae

(102)

(103)

in 100% yield.
(3) 119.5 g (0.5 mole) of N-methylol-β-diethyloxyphosphonopropionic acid amide are reacted with 35.5 g (0.5 mole) of acrylic amide as in Direction 1a), to give the compound of formula

(104)

in 100% yield.
Analysis: calculated: P 10.6 found P 10.3.
(4) 1 g of hydroquinone monomethyl ether and 101 g (1 mole) of methylolacrylic amide are dissolved in 249 g of triethylphosphite. The reaction mixture is heated to 100° C. A rapid rise in temperature to 140° C. ensures and ethanol and triethylphosphite distill off. After the temperature has fallen again to 100° C. after 2 hours, excess ethyl alcohol and unreacted triethylphosphite are distilled off from the reaction mixture in vacuo to give 220 g of the compound of formula

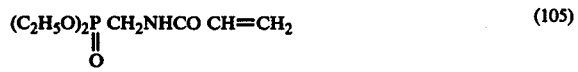
(105)

in 100% yield.
Analysis: calculated: C 43.4 H 7.3 N 6.3 P 14.0 found: C 43.4 H 7.6 N 5.9 P 14.0
(5) 85 g (1 mole) of methacrylic amide and 0.2 g of hydroxyquinone monomethyl ether are dissolved in 1000 ml of benzene. To this solution are added 30 g of para-formaldehyde. The solution is then warmed to 40° C. and a solution of 105 g (1 mole) of diethanolamine in 300 ml of benzene is added in the course of about 2 hours. The reaction mixture is then kept for a further 5 hours at 60° C. Upon termination of the reaction, the resultant compound precipitates as lower phase. It is isolated and freed from residual solvent, to give 178.5 g of a light yellow viscous compound of formula

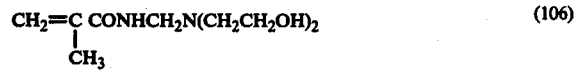
(106)

in 88.9% yield.
Analysis: calculated: N 13.85 found: N 13.4.
(6) 165 g (1 mole) of 2-glycidyltoluene and 3 g of sodium acetate (dry) are dissolved in 500 ml of ethyl acetate. To this solution are added 86 g (1 mole) of methacrylic acid, stabilised with 0.1 g of hydroquinone monomethyl ether and dissolved in 100 ml of ethyl acetate. After a 5 hour reaction at 50° C. the reaction mixture is cooled to room temperature and then filtered. The solvent is subsequently distilled off at 50° C. in vacuo, to leave as residue 224.6 g of the compound of formula

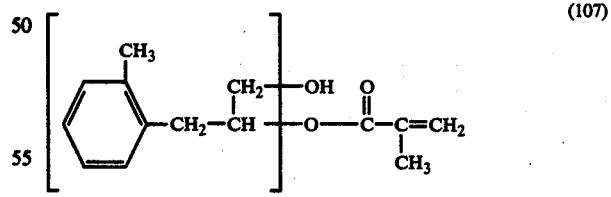
(107)

in 89.8% yield.
Analysis: calculated: C 70.8 H 7.3 found: C 69.9 H 7.4
The compound contains no epoxide groups.
(7) 23.4 g (0.1 mole) of phenylphenolsulphone (mixture of o- and p-phenylphenolsulphone) and 1 g of sodium acetate are dissolved in 50 ml of ethyl acetate. To this solution is added a solution of 14.2 g (0.1 mole) of glycidyl methacrylate (stabilised with 0.1 g of hydroquinone monomethyl ether) in 20 ml of ethyl acetate. After it has reacted for 12 hours at 50° C., the reaction mixture is cooled to room temperature and then filtered. The solvent is subsequently distilled off at 50° C. in vacuum to leave as residue 36.5 g of the compound of formula (108)

further 3 hours, to give 710 g of a viscous, colourless polymer emulsion (solids content: 15.5%).
Polymer yield: 96.5%.

The following copolymers are obtained by carrying out the procedure of Direction 9a):

Table 1

| No. | monomer I | monomer II | polymer yield in g | solids content in % | polymer yield in % |
|---|---|---|---|---|---|
| 9b | 100.2 g (0.3 mole) compound (103) | 48.2 g (0.1 mole) MPA$_1$ | 1140 | 12.8 | 94.8 |
| 9c | 33.4 g (0.1 mole) compound (103) | 144.6 g (0.3 mole) MPA$_1$ | 1300 | 13.4 | 95.7 |
| 9d | 165.5 g (0.5 mole) compound (103) | 48.2 g (0.1 mole) MPA$_1$ | 1420 | 14.0 | 93.3 |
| 9e | 139 g (0.5 mole) compound (101a) | 48.2 g (0.1 mole) MPA$_1$ | 1250 | 13.6 | 90.7 |
| 9f | 146 g (0.5 mole) compound (102) | 48.2 g (0.1 mole) MPA$_1$ | 1300 | 13.7 | 91.3 |
| 9g | 132 g (0.5 mole) compound (101b) | 48.4 g (0.1 mole) MPA$_1$ | 1192 | 16.02 | 97.5 |
| 9h | 44.2 g (0.2 mole) compound (105) | 19.3 g (0.04 mole) MPA$_2$ | 456 | 14.6 | 95.7 |

Table 2

| No. | monomer I | monomer II | monomer III | monomer IV | polymer yield (g) | solids content % | polymer yield (%) |
|---|---|---|---|---|---|---|---|
| 9i | 528g(2mole) compound(101b) | 193g(0.4mole) MPA$_1$ | 15g(0.13mole) MAME | — | 4524 | 15.8 | 96.3 |
| 9k | 80g(0.25mole) compound(102) | 31.4g(0.065mole) MPA$_1$ | 10g(0.087mole) MAME | — | 805 | 12.72 | 95.0 |
| 9l | 52.8g(0.2mole) compound(101b) | 19.3g(0.04mole) MPA$_1$ | 4.5g(0.02mole) compound(107) | — | 678 | 10.0 | 93.4 |
| 9m | 52.8g(0.2mole) compound(101b) | 1903g(0.04mole) MPA$_1$ | 15.04g(0.04mole) compound(108) | — | 734 | 10.7 | 98.4 |
| 9n | 52.8g(0.2mole) compound(101b) | 48.4g(0.1mole) MPA$_2$ | 10.4g(0.1mole) styrene | — | 771 | 13.5 | 93.7 |
| 9o | 44.2g(0.2mole) compound | 19.3g(0.04mole) MPA$_1$ | 1.15g(0.01mole) MAME | — | 477 | 13.8 | 98.02 |
| 9p | 52.8g(0.2mole) compound(101b) | 48.4g(0.1mole) MPA$_1$ | 10.4g(0.1mole) styrene | 10.4g(0.01 mole)methylmethacrylate | 805 | 16.7 | 88.0 |

MPA$_1$ = ω-methoxypolyethylene glycol acrylate [CH$_3$O(CH$_2$CH$_2$O)$_{6-10}$COCH=CH$_2$]
MPA$_2$ = ω-methoxypolyethylene glycol acrylate [CH$_3$O(CH$_2$CH$_2$O)$_{10-15}$COCH=CH$_2$]
MAME = N-methylolacrylic amide monomethyl ether

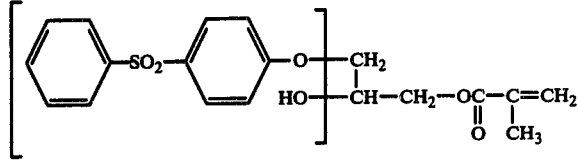

in 97% yield.
Analysis: calculated: C 60.6 H 5.3 S 8.5 found: C 58.4 H 5.3 S 9.3
The compound contains no epoxide groups.

(8) 33.4 g (0.1 mole) of the compound of formula (103) and 21 g (0.1 mole) of the compound of formula (106) are emulsified in 214 ml of water in the presence of 0.2 g of sodium lauryl sulphate as emulsifier. The polymerisation is initiated by adding 0.1 g of potassium persulphate and then carried out at 72° C. After 5 hours 0.1 g of potassium persulphate is again added and the polymerisation is terminated after a further 3 hours, to give 238 g of a colourless polymer solution of low viscosity (solids content=18.4), corresponding to a polymer yield of 90%.

(9a) 33.4 g (0.1 mole) of the compound of formula (103) and 48.2 g (0.1 mole) of ω-methoxypolyethylene glycol acrylate (molecular weight ~ 482) are emulsified in 635 ml of water in the presence of 7.2 g of sodium lauryl sulphate. The polymerisation is initiated by addition of 0.2 g of potassium persulphate and then carried out at 75° C. After 4 hours 0.2 g of potassium persulphate is again added and the polymerisation is terminated after a (10a) The procedure of Manufacturing Direction 9a) is repeated using a solution of 10 g of methylolacrylic amide monomethyl ether in 50 ml of deionised water after a polymerisation time of 3 hours. After a further hour 0.2 g of potassium persulphate is added and the polymerisation is then terminated after 3 hours, to give 756 g of a viscous, colourless polymer emulsion (solids content: 23.2%), corresponding to a polymer yield of 97.8%.

(10b) The procedure of Manufacturing Direction 9a) is repeated using 52.8 g (0.2 mole) of the compound of formula (101b), 24.5 g (0.04 mole) of a ω-methoxypolyethylene glycol acrylic acid ester [CH$_3$O(CH$_2$C-H$_2$O)$_{10-15}$COCH=CH$_2$] and 1.15 g (0.01 mole) of methylolacrylic amide monomethyl ether, to give 455 g of a viscous, colourless polymer emulsion (solids content: 15.8%).
Polymer yield: 95.5%.

(11) 20.2 g (0.1 mole) of compound (106) and 33.4 g (0.1 mole) of compound (103) are dissolved in 180 ml of water and polymerised for 24 hours at 50° C. in the presence of 0.2 g of potassium persulphate, to give 226 g of a viscous emulsion which, after filtration, has a solids content of 21.4%.
Polymer yield: 93.8%.

A storable emulsion with a pH of 7 is obtained by adding 5 g of polyacrylic acid.

(12a) Copolymer of isobutylacrylate/methylmethacrylate/methacrylic amide-N-methylol monomethyl ether. 55.2 g (0.4 mole) of isobutylacrylate are dissolved in 150 ml of water and in the presence of 1 g of sodium lauryl sulphate. The polymerisation is initiated by addition of 0.1 g of potassium persulphate. Then 10 g (0.1 mole) of methylmethacrylate are added in the course of 35 minutes and the polymerisation is continued for 4½ hours at 75° C. Then 2 g (0.015 mole) of methacrylic amide-N-methylol monomethyl ether, dissolved in 100 ml water, and 0.2 g of potassium persulphate are added and the polymerisation is brought to completion after a further 3 hours at 85° C., to give 314 g of a viscous emulsion with a solids content of 21% (corresponding to a polymer yield of approx. 100%).

Copolymers are obtained from the following monomers in analogous manner:

(b) 2 parts of isobutylacrylate
  1.4 parts of methylmethacrylate
  1 part of acrylic acid
(c) 5 parts of isobutylacrylate
  1 part of methylmethacrylate
  2 parts of methacrylic amide-N-methylol monomethyl ether
(d) 2 parts of isobutylacrylate
  1 part of methylacrylate
  1 part of acrylic acid.

(13) 105.5 g (0.5 mole) of methylol-β-dimethoxyphosphonopropionic acid amide and 120.5 g of cetylamine (0.5 mole) are dissolved in 1000 ml of dioxan and the solution is heated for 10 hours to 100° C. (reflux). The solvent is subsequently distilled off in a water-jet vacuum to give 224 g of a wax-like compound of formula

 (109)

in 99% yield.

Analysis: calculated: N 6.45 P 7.12 found: N 6.22 P 7.52

Mass spectrum: M = 434 (theory: 434).

(14) The procedure of Direction 13) is repeated using 134.5 g (0.5 mole) of stearylamine in place of cetylamine to give 229 g of a wax-like compound of formula

 (110)

in 99.1% yield.

Analysis: calculated: N 6.06 P 6.70 found: N 5.95 P 6.70

Mass spectrum: M = 462 (theory: 462).

(15) The procedure of Direction 13) is repeated using 92.5 g (0.5 mole) of laurylamine in place of laurylamine to give 175.4 g of a wax-like compound of formula

 (111)

in 92.8% yield.

Analysis: calculated: N 7.4 P 8.2 found: N 7.3 P 8.7
Mass spectrum: M = 378 (theory: 378).

(16) The procedure of Direction 13) is repeated using 120.5 g (0.5 mole) of di-2-ethylhexylamine in place of cetylamine to give 188.5 g of a compound of formula

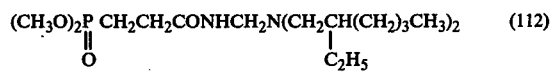 (112)

in 95.7% yield.

Analysis: calculated: N 6.45 P 7.12 found: N 6.22 P 6.4

Mass spectrum: M = 434 (theory: 434).

(17) The procedure of Direction 13) is repeated using 133.5 g (0.5 mole) of methylol-β-diisopropoxyphosphonopropionic acid amide and 134.5 g (0.5 mole) of stearylamine to give 235 g of a compound of formula

 (113)

in 96.5% yield.

Analysis: calculated: N 5.04 P 5.97 found: N 5.5 P 6.1
Mass spectrum: M = 518 (theory: 518).

(18) The procedure of Direction 13) is repeated using 133.5 g (0.5 mole) of methylol-β-diisopropoxyphosphonopropionic acid amide and 120.5 g of hexadecylamine (0.5 mole), to give 235 g of a compound of formula

 (114)

in 96% yield.

Analysis: calculated: N 5.71; P 6.31; found: N 5.7; P 6.5.

Mass spectrum: M = 490 (theory: 490).

(19) The procedure of Direction 13) is repeated using 133.5 g (0.5 mole) of methylol-β-diisopropoxyphosphonopropionic acid amide and 260.5 g (0.5 mole) of stearylamine, to give 378 g of the compound of formula

 (115)

in 98.2% yield.

Analysis: calculated: N 3.63; P 4.02; found: N 3.8; P 3.9.

Mass spectrum M = 770 (theory: 770).

(20) 73.5 g (0.5 mole) of phthalimide are reacted with 15 g (0.5 mole) of formaldehyde and 92.5 g (0.5 mole) of laurylamine in benzene for 10 hours at 80° C. as in Direction 13). The solvent is subsequently distilled off in a water-jet vacuum.

Yield: 168 g (=97.7%) of the compound of formula

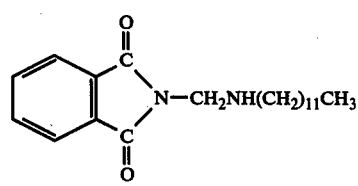 (116)

Analysis: calculated: N 8.14 found: N 8.0
Mass spectrum: M = 344 (theory: 344).

(21) 73.5 g (0.5 mole) of phthalimide are reacted with 15 g (0.5 mole) of formaldehyde and 120.5 g (0.5 mole) of cetylamine as in Direction 20).

Yield: 198 g (=99%) of the compound of formula

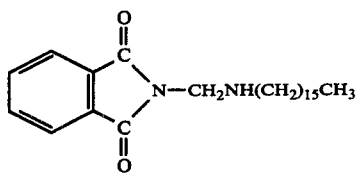 (117)

Analysis: calculated: N 7.0; found: N 7.3.
Mass spectrum: M = 400 (theory: 400).
(22) 56.5 g (0.5 mole) of caprolactam are reacted with 15 g (0.5 mole) of formaldehyde and 92.7 g (0.5 mole) of laurylamine as in Direction 20).
Yield: 146.6 g (=94.7%) of the compound of formula

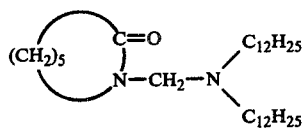 (118)

Analysis: calculated: N 9.02 found: N 8.75
Mass spectrum: M = 310 (theory: 310).
(23) 56.5 g (0.5 mole) of caprolactam are reacted with 15 g (0.5 mole) of formaldehyde and 92.5 g (0.5 mole) of laurylamine as in Direction 20), to give 146.6 g of the compound of formula

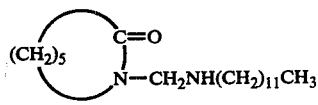 (119)

in 94.7% yield.
Analysis: calculated: N 9.02 found: N 8.75
Mass spectrum: M = 310 (theory: 310).
(24) 73.5 g (0.5 mole) of phthalimide are reacted with 15 g (0.5 mole) of formaldehyde and 285.5 g (0.5 mole) of stearylamine as in Direction 20).
Toluene is used as solvent.
Yield: 332 g (=97.1%) of the compound of formula

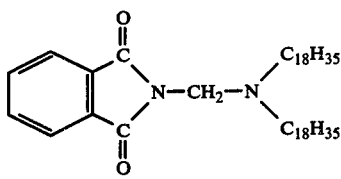 (120)

Analysis: calculated: N 4.4 found: N 4.2.
(25) 56.6 g (0.5 mole) of caprolactam are reacted with 15 g (0.5 mole) of formaldehyde and 120.5 g (0.5 mole) of cetylamine as in Direction 20), with toluene as solvent, to give 178 g of the compound of formula

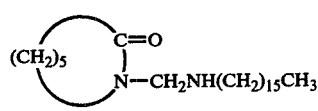 (121)

in 97% yield.
Analysis: calculated: N 7.64 found: N 7.1
Mass spectrum: M = 366 (theory: 366).
(26) 49.5 g (0.5 mole) of succinimide are reacted with 15 g (0.5 mole) of formaldehyde and 92.5 g (0.5 mole) of laurylamine as in Direction 20), with toluene as solvent, to yield 115 g of the compound of formula

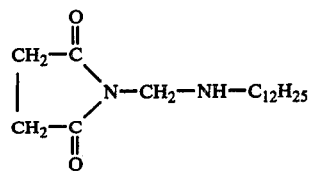 (122)

in 83.94% yield.
Analysis: calculated: N 9.45; found: — N 9.2.
(27) 49.5 g (0.5 mole) of succinimide are reacted with 15 g (0.5 mole) of formaldehyde and 120.5 g (0.5 mole) of cetylamine as in Direction 20), with toluene as solvent, to yield 176 g of the compound of formula

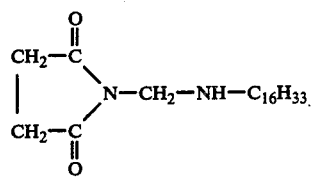 (123)

in 100% yield.
Analysis: calculated: N 7.95 found: — N 7.2
(28) 98.5 g (0.5 mole) of laurinolactam are reacted with 15 g (0.5 mole) of formaldehyde and 92.5 g (0.5 mole) of laurylamine as in Direction 20), with toluene as solvent, to give 197 g of the compound of formula

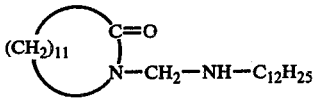 (124)

in 100% yield:
Analysis: calculated: N 7.1 found: N 7.5.
(29) The following mixtures of copolymers - obtained according to Direction 9a) - and further monomers are prepared:

| | copolymer | monomeric compound | solids content of the mixture in % |
|---|---|---|---|
| a) | 55.6 g (0.02 mole) of the compound of formula (101a) 19.3 g (0.04 mole) of MPA$_2$ 1.5 g (0.01 mole) of MAME | 4.4 g (0.01 mole) of the compound of formula (109) | 16 |
| b) | as a) | 4.6 g (0.01 mole) of the compound of the formula (110) | 15.5 |
| c) | as a) | 4 g (0.11 mole) of the compound of formula (121) | 16 |
| d) | 27.8 g (0.1 mole) of the compound of formula (101a) 20.2 g (0.1 mole) of the compound of formula (106) 20 g (0.2 mole) of methylmethacrylate | 4.4 g (0.01 mole) of the compound of formula (109) | 10 |
| e) | 55.6 g (0.2 mole) of the compound of formula (101a) 19.3 g (0.04 mole) of MPA$_2$ | 4.4 g (0.01 mole) of the compound of formula (109) | 15.5 |

EXAMPLE 1

The following preparations are prepared and padded on polyamide carpets at room temperature. The carpets are squeezed out to a weight pick-up of 100%. The finished carpets are subsequently dried for 30 seconds at 170° C. Preparations (the parts denote the solids content of the respective polymer):

A. 50 g/l of the polymer emulsion of Direction 11)
B. 35.8 g/l of an emulsion consisting of 66.8 parts of the polymer obtained in Direction 8)
   56.3 parts of the polymer obtained in Direction 9a), and
   67.9 parts of the polymer obtained in Direction 12a)
C. 50 g/l of an emulsion consisting of
   60.4 parts of the polymer obtained in Direction 9e) and
   121.2 parts of the polymer obtained in Direction 11)
D. 1 part of the copolymer of Direction 12b)
   1 part of the copolymer of Direction 9e)
   2.5 parts of the copolymer derived from 1 parts of the monomer obtained in Direction 1a) and 1 part of the monomer obtained in Direction 5)
E. 1 part of the copolymer obtained in Direction 9b)
   1.25 parts of the copolymer derived from 1 part of the monomer obtained in Direction 1a) and 1 part of the monomer obtained in Direction 5)
F. 2 parts of the copolymer obtained in Direction 2c)
   1.5 parts of the copolymer obtained in Direction 9e)
   2 parts of the copolymer derived from 1 part of the monomer obtained in Direction 1a) and 1 part of the monomer obtained in Direction 5)
G. 1 part of the copolymer obtained in Direction 12c)
   1 part of the copolymer obtained in Direction 9e)
   1 part of the polymer obtained from the monomer obtained in Direction 5)
   1 part of the copolymer obtained in Direction 12d)
H. 1 part of the copolymer obtained in Direction 12d)
   1 part of the polymer obtained from the monomer prepared in Direction 5)
   1 part of the copolymer obtained in Direction 9e).

The parts referred to in the mixtures D. to H. refer to "parts of aqueous emulsion with 10% solids content" of the indicated homopolymers or co-polymers. The results are reported in Table III.

Table III

|  | A | B | C | D | E | F | G | H |
|---|---|---|---|---|---|---|---|---|
| fastness to rubbing (dry): | 5 | 5 | 4 | 5 | 4–5 | 5 | 5 | 5 |
| (wet): | 4 | 5 | 4 | 4–5 | 4–5 | 5 | 4 | 4–5 |
| handle | soft | soft | soft | soft | soft | soft | soft | soft |
| antistatic effect | good | very good | very good | very good | very good | very good | very good | very good |
| antisoil effect (dry): |  |  |  |  |  |  |  |  |
| treated | 3 | 3 | 3 | 3 | 3 | 3 | 3 | 3 |
| untreated | 2–3 | 2–3 | 2–3 | 2–3 | 2–3 | 2–3 | 2–3 | 2–3 |

The fastness to rubbing is evaluated by the rating 1 to 5 (maximum rating = 5)
The antisoil effect is evaluated by means of a grey Scale (1 to 5), in which the highest rating is 5.

EXAMPLE 2

(a) A polyamide carpet is padded at room temperature with the following preparations and squeezed out to a weight pick-up of 100%. The finished carpet is then dried for 30 seconds at 170° C.
Preparation (the amounts in g/l indicate the solids content):
A. 50 g/l of the mixture consisting of 1 part of the compound of formula (121) and 4 parts of the aqueous emulsion prepared according to Direction 9d) (solids content 10%)
B. 85.5 g/l of the mixture consisting of 20 parts of the emulsion (20 g/l) of the compound of formula (109) and 80 parts of the polymer emulsion prepared in Direction 9a)
C. 15 g/l of the mixture according to B.

The following results are obtained:

Table IV

|  | A | B |
|---|---|---|
| fastness to rubbing (dry): | 5 | 4 |
| (wet): | 4 | 4 |
| handle | soft | soft |
| antistatic effect | very good | very good |
| antisoil effect (dry): |  |  |
| treated | 4 | 3–4 |
| untreated | 3 | 3 |

(b) Different fabrics are padded at room temperature with preparation C (15g/l of the mixture according to B), squeezed out and dried as described in a).
The antisoil effect is determined by reflection measurement (determination of the whitening (−) or greying (+) compared with untreated material).

Table V

| fibrous material (wovens) | handle | antistatic effect | antisoil treated | effect dry untreated |
|---|---|---|---|---|
| polyamide | medium soft | good | 6.5(−) | 0 |
| polyacrylnitrile | medium soft | very good | 3.1(−) | 0 |
| polyester | medium soft | very good | 3.1(−) | 0 |
| polyester/cotten (65/35) | medium soft | — | 4.1(+) [2.6 (+) after 5 washes] | 0 |

EXAMPLE 3

Polyamide carpets are padded at room temperature with aqueous (unless indicated to the contrary) treatment liquors at room temperature to a weight pick-up of 100%. The treated carpets are subsequently dried for 10 minutes at 150° C.
The results are reported in Table VI.
Preparations:
1. 50 g/l of an emulsion consisting of
   100 parts of the compound of formula (109)
   35 parts of the compound of formula (119)
   140 parts of the copolymer of Direction 9c)
2. 30 g/l of preparation 1
3. 50 g/l of an emulsion consisting of
   10 parts of the compound of formula (114)
   128 parts of the copolymer prepared in Direction 9b)
4. 50 g/l of an emulsion consisting of
   10 parts of the compound of formula (109)
   10 parts of the compound of formula (119)
   136 parts of the copolymer prepared in Direction 9e)
5. 50 g/l of an emulsion consisting of 10 parts of the compound of formula (109)
136 parts of the copolymer prepared in Direction 9*l*)
6. 50 g/l of the emulsion obtained according to Direction 9g)
7. 68.4 g/l of the emulsion obtained according to Direction 9h)
8. 62.4 g/l of the emulsion obtained according to Direction 9i)
9. 78.8 g/l of the emulsion obtained according to Direction 9k)
10. 100 g/l of the emulsion obtained according to Direction 9l)
11. 74.6 g/l of the emulsion obtained according to Direction 9m)
12. 74.6 g/l of the emulsion obtained according to Direction 9n)
13. 72.4 g/l of the emulsion obtained according to Direction 9o)
14. 72.8 g/l of the emulsion obtained according to Direction 9p)

Colour, handle and soil tendency are indicated in comparison with untreated material.

I claim:

1. A method of providing synthetic organic fibrous material with an antistatic and dirt repellent finish which comprises treating said material with an aqueous or organic solution or emulsion containing 1–30 percent by weight of a composition consisting essentially of a 75 to 100 percent by weight of a copolymer having a molecular weight between about 2,000 and 50,000 of at least two monomers in a ratio of about 1:10 to 10:1 and of the formulae

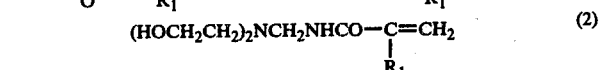

and

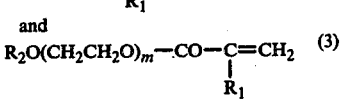

Table VI

| preparation | fastness to rubbing | | colour | handle | soil tendency (compared with untreated material) | electrostatic behaviour | |
|---|---|---|---|---|---|---|---|
| | dry | wet | | | | resistance Ω | max.charge (volt) |
| 1 | 4 | 4 | white | soft | slighter | $1.7 \cdot 10^{11}$ | 2–332 |
| 2 | 4 | 3–4 | white | soft | same | $1.5 \cdot 10^{11}$ | 139–297 |
| 3 | 5 | 4–5 | white | as untreated | as untreated | $8.2 \cdot 10^{11}$ | 810–1600 |
| 4 | 4–5 | 4 | white | as untreated | as untreated | $5.9 \cdot 10^{10}$ | 200–780 |
| 5 | 4–5 | 3 | as untreated | as untreated | as untreated | $4.4 \cdot 10^{10}$ | 270–800 |
| 6 | 4,5 | 4 | as untreated | as untreated | as untreated | $2.2 \cdot 10^{11}$ | 360–899 |
| 7 | 4.5 | 4.5 | as untreated | as untreated | as untreated | $1.2 \cdot 10^{11}$ | 70–460 |
| 8 | 4.5 | 4 | as untreated | as untreated | as untreated | $7.0 \cdot 10^{10}$ | 300–1095 |
| 9 | 5 | 4 | as untreated | somewhat harder | somewhat stronger | $1.8 \cdot 10^{11}$ | 750–1430 |
| 10 | 5 | 5 | as untreated | as untreated | somewhat stronger | $1.1 \cdot 10^{10}$ | 10 |
| 11 | 4.5 | 4.5 | as untreated | softer | somewhat stronger | $3.5 \cdot 10^{10}$ | 10 |
| 12 | 5 | 4.5 | as untreated | as untreated | somewhat stronger | $9.6 \cdot 10^{10}$ | 38–440 |
| 13 | 5 | 4.5 | as untreated | softer | somewhat stronger | $2.5 \cdot 10^{11}$ | 570–1380 |
| 14 | 5 | 5 | as untreated | as untreated | somewhat stronger | $2.9 \cdot 10^{10}$ | 10–200 |

The resistance [Ω] for untreated material is $10^{13}$; the maximum charge is approximately 1000 volts.

EXAMPLE 4

Polyamide carpets are treated with the mixtures of Manufacturing Direction 29) (in each case 50 g/l of the mixtures, 80 g/l in 29d) as in Example 3. The results obtained are reported in Table VII.

or mixtures of such copolymers wherein
R is straight-chain or branched alkyl of 1 to 8 carbon atoms, Table VII

| preparation | 29a | 29b | 29c | 29d | 29e |
|---|---|---|---|---|---|
| fastness to rubbing: dry | 4.5 | 4.5 | 4.5 | 4.5 | 4.5 |
| wet | 4 | 4 | 4 | 4.5 | 4 |
| colour | as untreated | as untreated | as untreated | as untreated | as untreated |
| handle | somewhat softer | as untreated | as untreated | as untreated | softer |
| soil tendency | as untreated | slighter | as untreated | slighter | as untreated |
| electrostatic behaviour: resistance | $1.3 \cdot 10^{11}$ | $2.2 \cdot 10^{11}$ | $1.8 \cdot 10^{11}$ | $1.0 \cdot 10^{11}$ | $6.4 \cdot 10^{10}$ |
| maximum charge (volts) | 115–380 | 1940–3420 | 820–1590 | 950–1590 | 40–360 |

$R_1$ is hydrogen or methyl,
$R_2$ is alkyl of 1 to 6 carbon atoms,
$m$ is an integer from 6 to 15 and each of $r$ and $s$ is 1 or 2;

or said copolymer of at least two of (1), (2) and (3) containing an additional monomer in a ratio of about 1:10 to 10:1 and selected from the group consisting of vinyl esters of organic acids, vinyl alkyl ketones, vinyl halides, acrylic nitrile or acrylic amide and derivatives thereof, which are substituted at the amide nitrogen and $\alpha,\beta$-unsaturated mono- or dicarboxylic acids containing 3 to 5 carbon atoms and esters thereof; and b. 25 to 0 percent by weight of at least one of
$b_1$. a homopolymer of (1), (2) or (3) having a molecular weight of about 2,000 to 50,000;
$b_2$. a homopolymer or copolymer of vinyl esters of organic acids, vinyl alkyl ketones, vinyl halides, acrylic nitrile or acrylic amide or derivatives thereof which are substituted at the amide nitrogen, or $\alpha,\beta$-unsaturated mono- or dicarboxylic acids containing 3 to 5 carbon atoms or esters thereof, and having a molecular weight between about 2,000 and 50,000;
$b_3$. a compound of the formula

  (4)

wherein R' is straight-chain or branched alkyl of 1 to 18 carbon atoms, $R_1$ is hydrogen or methyl, $R_2'$ is hydrogen or $C_nH_{2n+1}$ and $n$ is an integer from 1 to 24; and $b_4$. a compound of the formula

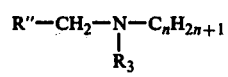  (5)

wherein R" is

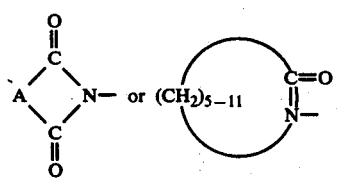

wherein A is $-CH_2CH_2-$, $-CH=CH-$ or

$R_3'$ is hydrogen or $C_nH_{2n+1}$ and $n$ is an integer from 1 to 24.

2. A method according to claim 1, wherein the composition contain at least one copolymer of at least two of the monomers of formulae

-continued

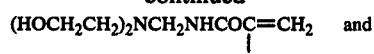

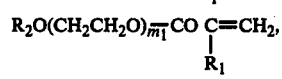

wherein $m_1$ in an integer from 6 to 10, or a copolymer of the cited monomers and further ethylenically unsaturated monomers.

3. A method according to claim 1, wherein the composition contains at least one copolymer of at least two of the monomers of formulae

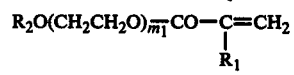

wherein $m_1$ is an integer from 6 to 10, in admixture with at least one compound of the formula

4. A method according to claim 1, wherein the composition contains at least one copolymer of at least two of the monomers of formula

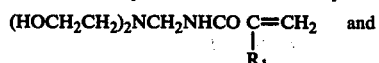

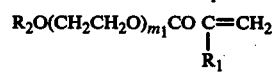

wherein $m_1$ is an integer from 6 to 10, or a copolymer of the cited momomers and further ethylenically unsaturated monomers, in admixture with at least one compound of formulae

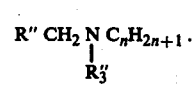

5. A method according to claim 1, wherein the monomers of (a) (1), (2) and (3) respectively are of

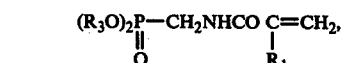

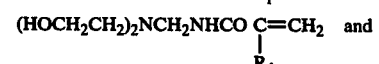

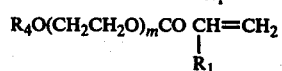

wherein $R_1$ is hydrogen or methyl, $R_3$ and $R_4$ are alkyl of 1 to 4 carbon atoms and $m$ is an integer from 6 to 15.

6. A method according to claim 5, wherein the copolymer of (a) is a copolymer of the monomers of formulae $$(R_3O)_2\underset{\underset{O}{\|}}{P}-CH_2NHCO-\underset{\underset{R_1}{|}}{C}=CH_2 \text{ and}$$

$$R_4O(CH_2CH_2O)_{\overline{m_2}}CO-\underset{\underset{R_1}{|}}{C}=CH_2$$

wherein $m_2$ is an integer from 10 to 15.

7. A method according to claim 1, wherein the copolymer is (a) is a copolymer of the monomers of formulae $$(RO)_2\underset{\underset{O}{\|}}{P}-CH_2\underset{\underset{R_1}{|}}{C}HCONHCH_2NHCO-\underset{\underset{R_1}{|}}{C}=CH_2 \text{ and}$$

$$(HOCH_2CH_2)_2NCH_2NHCO-\underset{\underset{R_1}{|}}{C}=CH_2.$$

8. A method according to claim 1, wherein the copolymer of (a) is a copolymer of the monomers of formulae $$(RO)_2\underset{\underset{O}{\|}}{P}-CH_2\underset{\underset{R_1}{|}}{C}HCONHCH_2NHCO-\underset{\underset{R_1}{|}}{C}=CH_2 \text{ and}$$

$$R_2O(CH_2CH_2O)_{\overline{m_1}}CO-\underset{\underset{R_1}{|}}{C}=CH_2$$

wherein $m_1$ is an integer from 6 to 10.

9. A method according to claim 1, wherein the copolymer of (a) is a copolymer of the monomers of formulae $$(HOCH_2CH_2)_2NCH_2NHCO-\underset{\underset{R_1}{|}}{C}=CH_2 \text{ and}$$

$$R_2O(CH_2CH_2O)_{\overline{m_1}}CO-\underset{\underset{R_1}{|}}{C}=CH_2,$$

wherein $m_1$ is an integer from 6 to 10.

10. A method according to claim 1, wherein the monomers of (a) (1), and (3) respectively are of the formulae $$(R_3O)_2\underset{\underset{O}{\|}}{P}-CH_2\underset{\underset{R_1}{|}}{C}HCONHCH_2NHCO-\underset{\underset{R_1}{|}}{C}=CH_2$$

$$(HOCH_2CH_2)_2NCH_2NHCO-\underset{\underset{R_1}{|}}{C}=CH_2 \text{ and}$$

$$R_4O(CH_2CH_2O)_{\overline{m_1}}CO-\underset{\underset{R_1}{|}}{C}=CH_2$$

wherein $R_1$ is hydrogen or methyl, $R_3$ and $R_4$ are alkyl of 1 to 4 carbon atoms and $m_1$ is an integer from 6 to 10.

11. A method according to claim 1, wherein the composition contains copolymers of the monomers of formulae (1) and (2) in admixture with copolymers of the monomers of formulae (1) and (3) and (3) of copolymers of the monomers of formulae (1) and (3) in admixture with copolymers of the monomers of formulae (2) and (3).

12. A method according to claim 1, wherein the composition contains copolymers of the monomers of formulae (1) to (3) in admixture with homopolymers of the monomers of formulae (1) to (3).

13. A method according to claim 1, wherein the additional monomers of (a) and the monomers of ($b_2$) are acrylic acid, methylmethacrylate, isobutylacrylate, methacrylic amide-N-methylol monomethyl ether, 2-ethylhexylacrylate, 3-toyl-2(1)-hydroxypropyl-1(2)-methacrylate and 2(1)-phenylphenolsulphone1(2)-hydroxypropylmethacrylate.

14. A method according to claim 1, wherein the component ($b_3$) is of the formula $$(R_5O)_2\underset{\underset{O}{\|}}{P}-CH_2\underset{\underset{R_1}{|}}{C}HCONHCH_2-\underset{\underset{R_6}{|}}{N}-C_{n_1}H_{2n_1+1}$$

wherein $R_5$ is alkyl of 1 to 4 carbon atoms, $R_1$ is hydrogen or methyl, $R_6$ is hydrogen, methyl or the radical $C_{n_1}H_{2n_1+1}$ and $n_1$ is an integer from 6 to 24.

15. A method according to claim 14, wherein the component ($b_3$) is of the formula $$(R_5O)_2\underset{\underset{O}{\|}}{P}-CH_2\underset{\underset{R_1}{|}}{C}HCONHCH_2NH-C_{n_2}H_{2n_2+1}$$

wherein $n_2$ is an integer from 6 to 18.

16. A method according to claim 1, wherein the component ($b_4$) is of the formula $$R''CH_2\underset{\underset{R_7}{|}}{N}\,C_{n_1}H_{2n_1+1}$$

wherein $R_7$ is hydrogen, methyl or the radical $C_{n_1}H_{2n_1+1}$ and $n_1$ is an integer from 6 to 24.

17. A method according to claim 16, wherein the component ($b_4$) is of the formula $$R''CH_2NH-C_{n_2}H_{2n_2+1}$$

wherein $n_2$ is an integer from 6 to 18.

18. A method according to claim 1, wherein the component ($b_4$) is of the formula

[structure: phthalimide-type ring with $N-CH-N$ bearing $C_nH_{2n+1}$ and $R_3'$]

or

[structure: caprolactam-type ring $(CH_2)_5$ with $C=O$, $N-CH_2-N$ bearing $C_nH_{2n+1}$ and $R_3'$]

wherein $R_3'$ is hydrogen or $C_nH_{2n+1}$ and $n$ is an integer from 1 to 24.

19. A method according to claim 1, which comprises applying the aqueous or organic solution or emulsion to the fibrous material at temperatures of 20° to 40° C.

20. A method according to claim 1, which comprises drying the finished textile material at 80° to 200° C.

21. The synthetic organic fibrous material finished by the method according to claim 1.

* * * * *